United States Patent [19]

Wiljan et al.

[11] Patent Number: 5,377,917
[45] Date of Patent: Jan. 3, 1995

[54] PROCESSING WASTE MATERIALS FOR ANAEROBIC DIGESTION OF THE BIOGENIC-ORGANIC CONSTITUENTS

[75] Inventors: Harry Wiljan; Ulrich Niefnecker, both of Munich; Ottokarl Muck, Berlin; Hans Kubler, Munich; Roland Schnell, Berlin; Roland Carra; Matthias Wild, both of Munich, all of Germany

[73] Assignee: REA Gesellschaft fur Recycling von Energie und Abfall mbH, Munich, Germany

[21] Appl. No.: 896,017

[22] Filed: Jun. 9, 1992

[30] Foreign Application Priority Data

Jun. 24, 1991 [DE] Germany ............................ 4120808

[51] Int. Cl.⁶ ............................................ B02C 23/00
[52] U.S. Cl. .................................... 241/14; 241/20; 241/21; 210/603
[58] Field of Search ............... 241/46.17, 20, 14, 21; 210/603

[56] References Cited

U.S. PATENT DOCUMENTS

| | | | |
|---|---|---|---|
| 3,595,488 | 7/1971 | Blakely et al. | 241/21 |
| 3,736,223 | 5/1973 | Marsh | 241/15 X |
| 3,788,568 | 1/1974 | Marsh | 241/46.17 X |
| 4,354,936 | 10/1982 | Ishida et al. | 210/603 X |
| 4,387,856 | 6/1983 | Selder | 241/46.17 X |
| 4,521,310 | 6/1985 | Casey | 210/603 |
| 4,565,552 | 1/1986 | Cotton | 210/603 X |
| 4,632,692 | 12/1986 | Lebesgue et al. | 210/630 X |
| 4,641,790 | 2/1987 | Musselmann et al. | 241/46.17 |
| 4,652,374 | 3/1987 | Cohen | 210/603 |
| 4,659,471 | 4/1987 | Molin et al. | 210/603 |
| 4,765,900 | 8/1988 | Schwoyer et al. | 210/603 |
| 4,953,457 | 9/1990 | Campo | 241/20 X |
| 5,015,384 | 5/1991 | Burke | 210/603 |
| 5,180,494 | 1/1993 | Yamaguchi et al. | 210/603 |
| 5,207,911 | 5/1993 | Pelligren et al. | 210/603 |

FOREIGN PATENT DOCUMENTS

| | | |
|---|---|---|
| 0126722A2 | 5/1984 | European Pat. Off. . |
| 0286100B1 | 4/1988 | European Pat. Off. . |
| 302852 | 8/1988 | European Pat. Off. . |
| 0291425 | 11/1988 | European Pat. Off. . |
| 2047006 | 9/1970 | Germany . |
| 2406404 | 2/1974 | Germany . |
| 3015239A1 | 4/1980 | Germany . |
| 3037714C2 | 10/1980 | Germany . |
| 3108923A1 | 3/1981 | Germany . |
| 3139914A1 | 10/1981 | Germany . |
| 3225026A1 | 7/1982 | Germany . |
| 3325504A1 | 7/1983 | Germany . |
| 3346476C2 | 12/1983 | Germany . |
| 3420433A1 | 6/1984 | Germany . |
| 3440754A1 | 11/1984 | Germany . |
| 3500132A1 | 1/1985 | Germany . |
| 3711813A1 | 4/1987 | Germany . |
| 3835230A1 | 10/1988 | Germany . |
| 3836379A1 | 10/1988 | Germany . |
| 3842138A1 | 12/1988 | Germany . |
| 3901404A1 | 1/1989 | Germany . |
| 3934478A1 | 10/1989 | Germany . |
| 3938464A1 | 11/1989 | Germany . |

Primary Examiner—Mark Rosenbaum
Assistant Examiner—Frances Han
Attorney, Agent, or Firm—Lowe, Price, LeBlanc & Becker

[57] ABSTRACT

In a process of treating waste materials for an anaerobic digestion of the biogenic organic constituents of the garbage, particularly of the source separated organic waste, the wet waste, the residual waste and the commercial wastes, an easily dewaterable suspension of the biogenic organic substances is formed in a pretreating stage by a mechanical treatment including a selective dissolution and defibration of the biogenic organic substances. In dependence on the adjusted solids concentration the action of flow-dynamical forces is so controlled that the not biogenic organic substances, are not subjected to an appreciable disintegration before they are removed at the end of the pretreatment. Non-digestable substances are removed. The suspension is converted to biogas by an anaerobic digestion and to a compost-like residue. In the apparatus in accordance with the invention a gentle treatment of adhering solids in the crude waste is ensured in the pretreating stage in that the speed of the impeller 14 in the pulping vessel 13 is controlled in dependence on the solids concentration. This will also result in a distinct saving of energy and in a high efficiency.

24 Claims, 5 Drawing Sheets

PROCESSING WASTE MATERIALS FOR ANAEROBIC DIGESTION OF THE BIOGENIC-ORGANIC CONSTITUENTS

BACKGROUND OF THE INVENTION

1. Field of the Invention

This invention relates to a process and an apparatus for treating waste for an anaerobic digestion of the biogenic organic constituents of the garbage, particularly the source separated organic waste, the wet waste, the residual waste and the commercial wastes.

2. Description of the Prior Art

The pretreatment and sorting of waste particularly of domestic and commercial waste have previously been effected almost exclusively by sorting means. The various fractions were intended to be separated without a substantial change of their moisture content. Conventional sorting comprises various combinations of disintegrating means, sieves, air-classifiers and means for hand-picking. An example of such means is disclosed in German Patent Specification 30 37 714.

It has also been proposed to process waste materials by a hydraulic separation, which may be performed as an independent process or as a process step in a sorting plant of the kind described hereinbefore.

For instance, published German Application 33 25 504 describes a process of treating and partly recycling domestic waste, bulky refuse, commercial waste material consisting mainly of garbage packaging material, and sewage sludge, as well as means for carrying out the process, in which the waste materials are initially disintegrated and separated into three sieve fractions. It has been proposed to fractionate the medium size fraction in that it is fed to a water-filled tub, in which heavy inorganic substances are intended to subside to the bottom whereas the light-weight substances rise to the surface so that they can be skimmed off and can be composted or subjected to anaerobic digestion.

A similar arrangement is described in published German Application 38 36 379, which relates to a process of treating the wet waste for the digestion of its organic content together with sewage sludge and an apparatus for a mechanical separation of organic and inorganic components of the refuse. In that case the medium size fraction which has been sieved off is treated by an apparatus in which spiked rollers are used to separate the organic and inorganic components.

Published German Application 35 00 132 describes the recovery and separation of organic components from the garbage in a process in which the light-weight components which have not been disintegrated are pneumatically separated from the mixed garbage by an air blast and are fed to a water pool, in which the heavy substances are caused to subside whereas the substances floating on the surface are carried by a weak current to discharge means.

But a separation of waste materials in stagnant or only slightly moving water will produce only unsatisfactory results. The settling velocity of the inorganic materials, particularly of the fines, is only low, and it is impossible to separate plastic materials with a density similar to organic constituents. For this reason it is taught in published German Application 35 00 132 that the waste materials which have risen to the surface should be boiled so that the structure of the organic substances will be destroyed to such a degree that they can be forced through a fine sieve and can be separated from the heat-resistant components, such as the plastics. But that process will require expensive equipment and has a high energy consumption.

A further disadvantage resides in that a very large amount of water in comparison with the amount of solids will be required for a separation in stagnant or slightly moved water and connection with the processes discussed no information has been furnished how the water which is laden with dissolved or suspended particulate organic and inorganic substances should be utilized or purified.

For preprocessing waste materials prior to a biotechnological process it is useful, particularly if a production of biogas is intended, to reduce the size of the organic substances before, after or during their separation in order to increase the reaction rate. In accordance with published German Application 38 36 379 a ball mill is used to disintegrate the organic fractions after their separation. It has been described in Published German Application 38 36 379 that the organic substances by disintegration in the ball mill will form a pulp so that the organic substances which have thus been disintegrated can then be utilized only in conventional biogas-plants with single phase digestion, as known from sewage sludge digestion or in agricultural biogas production.

The problems and operational restrictions involved in the operation of single-stage biogas-reactors have been explained in detail in the literature. It is known that much more efficient biogas-reactor system can be provided if the dissolution (hydrolysis) of the organic solids is effected prior to the methane production in a separate reactor system from which only the dissolved organic substances are fed into the methane reactor. Efficient reactor systems for the production of methane from dissolved organic substances are already commercially available.

But two-stage-digestion necessitates a highly efficient separation of organic from inorganic waste constituents. Those said organic substances need to be disintegrated in a way that their fibrous structure is preserved. This cannot be accomplished by the disintegrating means which have previously been used for size reduction of waste materials, particularly by the above-mentioned ball mill. But such a disintegration of the organic waste materials will inevitably result in a pulp so that it is difficult to remove the undissolved organic solids and that disintegration will unfavorably always involve an excessive reduction in size of the inorganic solids so that heavy metals will undesirably be entrained.

The above-mentioned sorting means are only of limited use for a separation of the non-digestable substances (glass, plastic sheeting and plastic containers, metals, stones, sand) because such substances are intimately blended with and adhesively bonded to the moist organic substances. For this reason said sorting and disintegrating means and the treating processes in which such means are employed cannot be used for a processing of waste materials to be subjected to biotechnological utilization.

A pulper may be used for a wet processing of waste materials without a need for previously sorting or disintegrating them. This has been described, e.g. in German Patent Specification 20 47 006. Mixed waste materials are continuously fed into the pulper, where they are simultaneously defibrated and disintegrated. Slurry is continuously withdrawn as a suspension through a perforate sieve. The defibration affects the biogenic organic waste materials, particularly the paper and cardboard materials, kitchen and yard waste. The impeller is so designed that all other substances will be broken or cut. Glass is to be crushed and aluminum is to be compacted to balls, which owing to relatively large perforation holes of the sieve are pumped off together with the fiber-containing slurry and are separated in subsequent process stages. Because the inorganic and metallic fractions are separated from the organic substances by hydrocyclones the pulper must be operated at a low solids concentration. Those non-digestable materials which cannot be defibrated or disintegrated pass through an opening in the bottom into a special separating and cleaning system, in which the fibers are separated for being recycled to the pulper.

In that case the disintegration of the inorganic non-digestable substances has a strong adverse effect on the quality of the fibrous organic substances because finely divided heavy metals will be released as a result of the disintegration and will enter the final product so that its use for agricultural soil amendment will be restricted or even precluded. A special disadvantage is involved in the crushing of glass because the sharp-edged particles of broken glass cause intense abrasion in pumps and pipes as well as congestions in tanks and pipes and may clog them.

A special problem arising in the processing of waste materials in a pulper is due to plastic materials in the form of large sheets and containers. In the processing of waste paper the nonbiological substances contained therein have such characteristic properties that cords and wires will form a rope, which is slowly withdrawn by means of a winch. But even in the processing of waste paper the content of the non-biological substances may be so high that that method will not be satisfactory. German Patent Specification 32 25 026 describes for that purpose a raking device which can allegedly be used for a reliable and continuous removal of coarse and heavy waste materials with a small expenditure of operating labor.

In the processing of waste, particularly of residual and commercial waste materials, it must be assumed that the sheet-like components (plastic sheeting) and the bulky ones (containers, bottles) cannot form a rope. For this reason published German Application 24 06 404 relating to a process of recovering recyclable components from waste material proposes to entrain the plastics out of the pulper by a partial stream of the suspension and to effect a separation into a fibre-containing suspension and non-biodegradable substances in a different, additional apparatus. In that case the suspension in the pulper is also required to operate at low solids concentration.

European Patent 0 286 100 discloses a process for the pretreatment and anaerobic digestion of biogenic organic waste and an apparatus for carrying out the process. In that process those fractions which are not biodegradable are first removed from the raw waste material. In a pretreating stage the biogenic organic fraction of the waste material is then softened by an addition of water or liquid waste material and is subjected at the same time to combined hydraulic and mechanical shearing actions to disintegrate the waste material whereas its fibrous structure is substantially preserved. This results in a raw suspension, which contains 3 to 15% by weight organic solids. In a succeeding alkaline pretreatment the raw suspension is adjusted to an alkaline state by adding chemicals and is heated to 40° to 60° C. and is held at that temperature for 2 to 12 hours. The suspension withdrawn from the alkaline pretreatment is subsequently divided in a solid-liquid separating stage into a liquid stream, which contains the water-soluble biological substances, and a solids-laden stream, which contains 20 to 50% by weight organic solids. The liquid stream is subsequently subjected to a methane fermentation and the solids-loaden stream is subjected to an anaerobic hydrolysis of solids under acid conditions and at a temperature in the mesophilic or thermophilic range and the resulting hydrolyzate is subjected to the methane fermentation. A pulper which can be used for the pretreatment has been disclosed in published German Application 37 11 813 of the same applicant.

The apparatus described there and its mode of operation for separating an organic fibrous fraction cannot be used to satisfactorily prepare said fibrous fraction for the succeeding anaerobic treatment and to recover the non-digestable substances in a way that they can be recycled respectively disposed of. That disadvantage will be the more significant the higher the content of the non-digestable substances in the waste material is to be processed because only a small part of the nondigestable substances floating in the suspension can be skimmed off during the pulping operation. The separation of the heavy substances is also unsatisfactory, particularly if the solids concentration in the suspension should be as high as possible. Besides, the non-digestable substances are accompanied by adhering fibrous substances, so that the materials must be aftertreated before they can be disposed of or recycled.

As a result, non-digestable substances cannot be removed unless the pulper is operated for a longer time than would be necessary only for the pulping and defibration of the organic substances. But the longer duration of the operation performed at high speed will increase the power consumption and the abrasion.

Whereas the separating effect could be improved in that the solids concentration in the suspension is decreased, this would undesirably require more expensive equipment and would increase energy requirement for the succeeding stages, particularly for the solid-liquid separation and the hydrolysis of solids.

SUMMARY OF THE INVENTION

It is an object of the invention to provide a process and an apparatus which are of the kind described first hereinbefore and can be used to separate the dissolved organic constituents and the organic fibrous materials from those substances which cannot be utilized by biotechnological processes, and to effect such a separation gently and with a high efficiency.

In the process and the apparatus in accordance with the invention the non-digestable substances which are not biogenic organic are subjected only to minor mechanical damage or size reduction and the separation of said solids is facilitated. Besides, the wear due to abrasive particulates inevitably formed by a crushing of brittle materials, such as glass, will be reduced.

Because the organic substances are pulped and defibrated in the pretreating stage, the fibrous suspension is withdrawn, the non-digestable substances are separated and these operations are effected in consecutive periods of time in a pulping vessel, which is specially provided for that purpose and which is integrated in a plant for producing biogas from the suspension thus obtained, the pretreatment will desirably involve low abrasion and relatively low energy consumption.

Because the non-digestable substances are entirely removed, the suspension can be digested to a higher degree in the succeeding process stages and an undesired inclusion of heavy metals in the compost-like residue which is formed by the process will be avoided.

Because the biogenic organic components are effectively separated from the crude material, the non-digestable substances which have been separated can be disposed of or recycled to a high degree.

DETAILED DESCRIPTION OF THE PREFERRED EMBODIMENT

The invention will now be described more in detail with reference to the accompanying drawings.

Figure 1:
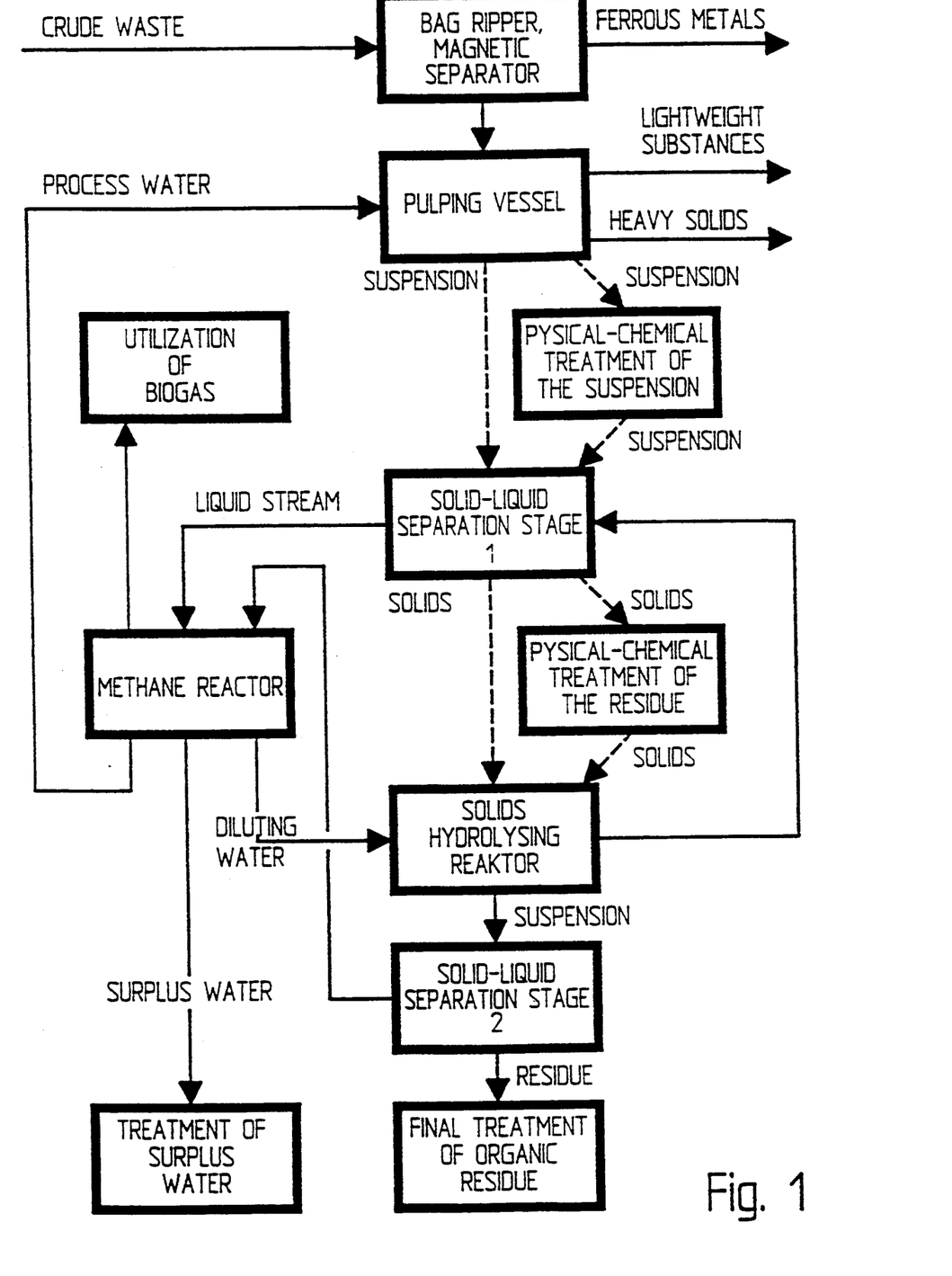
FIG. 1 is a flow scheme illustrating the consecutive steps of the process in accordance with the invention.

FIG. 1 is a flow scheme illustrating the process in accordance with the invention. Crude garbage consisting of biogenic organic substances and of non-digestable other substances is usually delivered in bags, which are opened by a bag ripper, in which the crude garbage is slightly predisintegrated and loosened. Thereafter, ferrous metals are separated by means of a magnetic separator and are recycled. The crude garbage from which the ferrous metals have substantially been removed is then fed to a pulping vessel, in which water, particularly process water, is added and the garbage is subjected to combined hydraulic and mechanical shearing forces to produce a crude suspension which is substantially free of non-digestable materials. When that suspension has been pumped off and the pulping vessel has been refilled with process water the heavy solids are withdrawn. The lightweight substances, that means those non-digestable substances which have a specific density differing only slightly from the density of water and therefore float in the water or rise to the surface, are removed and may optionally be subjected to a posttreatment to remove any adhering biogenic organic substances, such as fibres and the like.

The suspension which has been pumped off may optionally be subjected to a physical and/or chemical treatment under alkaline conditions and at an elevated temperature in order to increase the digestability of certain kinds of waste.

If that option is not adopted, the suspension will be transferred from the pulping vessel directly to a solid-liquid separating stage, in which the suspension is divided into a liquid stream and a stream containing the solids. That solid-liquid separation (1) will also be performed after the suspension has optionally been subjected to the physical and/or chemical treatment. The liquid stream which has been branched off contains the water-soluble substances and the solids-laden stream has a solids content of 20 to 50% by weight.

The liquid stream is fed to a methane reactor producing biogas. The effluent of the methane reactor is used in the pretreating stage as process water in the pulping vessel and as diluting water in the hydrolysis reactor. Surplus water is so treated that it can be discharged into the environment.

The stream containing the solids withdrawn from the first solid-liquid separating stage is then fed into the hydrolysis reactor either immediately or after the solids have been subjected to a physical and/or chemical treatment, e.g. with ozone, and in the hydrolysis reactor is mixed with diluting effluent water from the methane reactor. The suspension formed by the process of hydrolysis is returned to the solid-liquid separator (1), in which the hydrolyzate is separated from the non-hydrolyzed solids. The hydrolyzate is then fed into the methane reactor and the solids are returned to the hydrolysis reactor. That circulation through the solid-liquid separating stage (1) is continued until the processed hydrolyzate no longer contains a usable amount of dissolved organic substances.

When that state has been reached, those solids which can no longer be utilized in the process are supplied to a second solid-liquid separator, from which the solids are supplied to means for subjecting the residual organic substances to a final treatment consisting of an aerobic composting process. The liquid stream formed by the second solid-liquid separation is also fed into the methane reactor.

Figure 2:
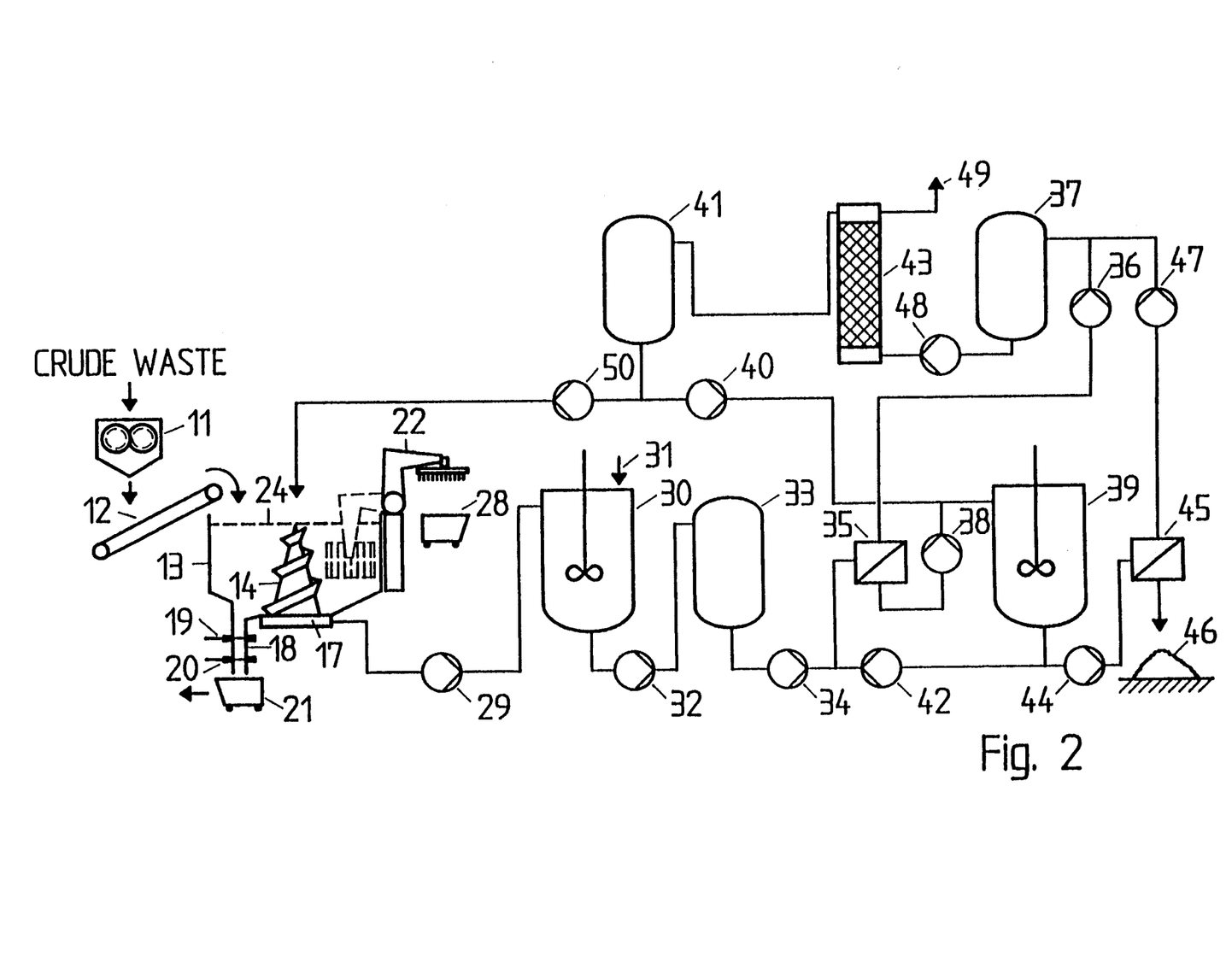
FIG. 2 is a schematic illustration showing the apparatus for carrying out the process with the associated parts of the apparatus and their cooperation.

In FIG. 2, components of the apparatus and their functional interconnection in the process are schematically shown. For this reason the several components of the apparatus will be described in a sequence which corresponds to the processing sequence. Crude waste usually delivered in waste bags is first passed through a bag ripper 11, by which the waste bags are torn open so that the components of the crude garbage are rendered more easily accessible. From the bag ripper 11 the crude garbage is delivered to a conveyor, such as a conveyor belt 12, and is charged by the latter in batches into a pulping vessel 13. Certain kinds of crude waste or waste materials may desirably be subjected to a sieving to remove fine inorganic non-digestable substances, a sorting to remove coarse and bulky objects or a separation of ferromagnetic materials by a magnet, before the waste is treated in the pulping vessel 13.

Figure 4:
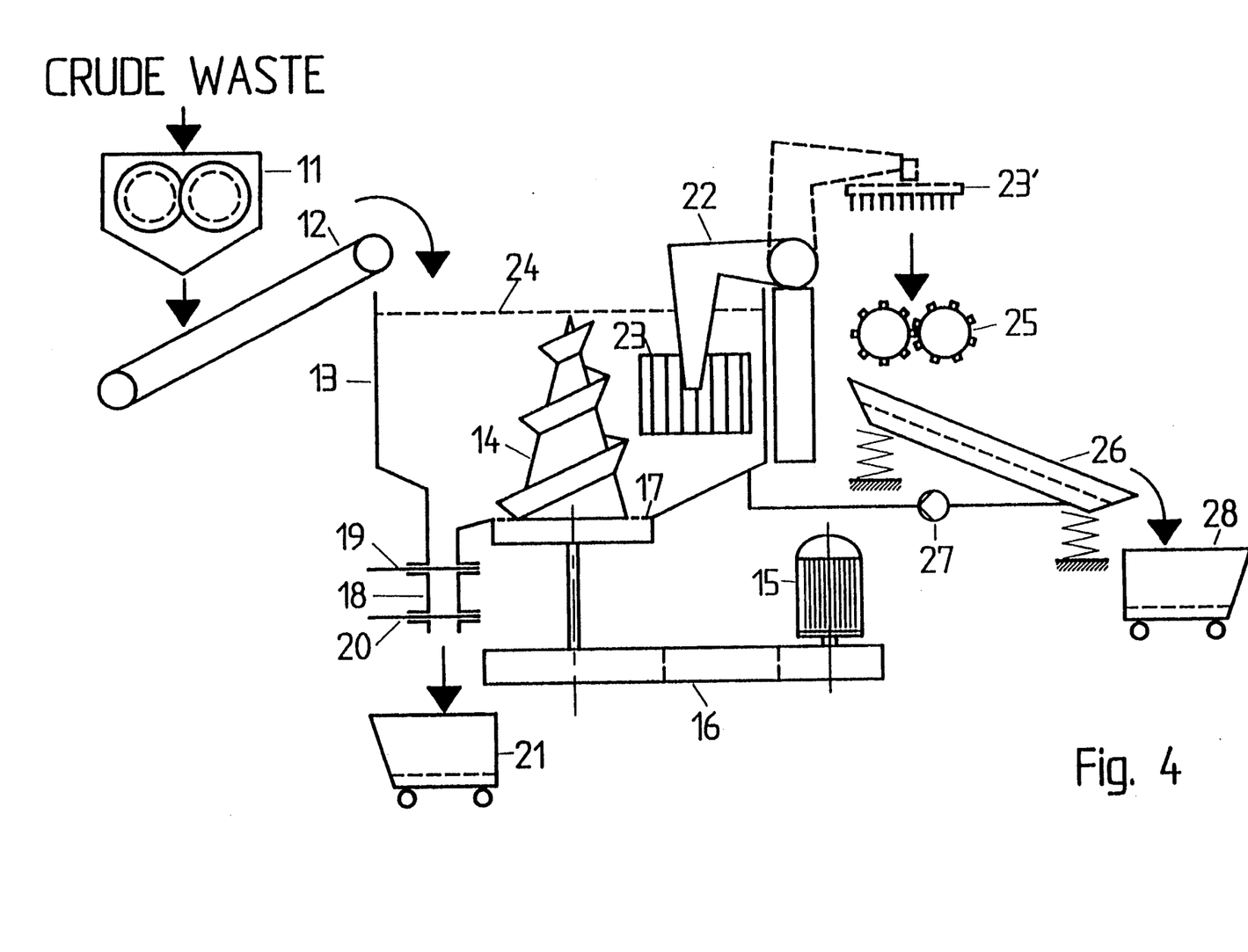
FIG. 4 is a schematic illustration showing the pulping vessel and the associated raking device.

The pulping vessel 13 is designed substantially like the pulper used to process waste paper. It comprises a central impeller 14, which rotates about a vertical axis and, as is shown in FIG. 4, is driven by a motor 15 and a V-belt 16 trained around belt pulleys. The speed of the motor and, in dependence thereon, the speed of the impeller can be adjusted to a certain predetermined value by an electronic control, not shown, during each period of the operation of the pulping vessel 13.

The pulping vessel 13 contains below the impeller 14 a centrally disposed perforate sieve 17 consisting of a sieve plate. The holes of the perforate sieve 17 are about 8 to 12 mm in diameter. A lock chamber 18 for heavy substances is provided at the bottom of the pulping vessel 13 and is defined by a top gate valve 19 and a bottom gate valve 20. A bin 21 for collecting the heavy substances and for carrying them away is disposed below the lock chamber 18 for heavy materials.

The impeller 14 is conical. A guide strip protruding from the shell of the impeller at about 45° extends spirally from the bottom end to the top end on the periphery of the cone. The rotation of the impeller 14 produces in the pulping vessel 13 a toroidal or loop-shaped flow in the suspension. That flow is radially outwardly directed at the bottom and has a small lateral flow component. The flow which is produced by the impeller 14 causes hydraulic shearing forces to be exerted in the suspension and said shearing forces result in a defibration of biogenic organic substances.

A raking device 22 is associated with the pulping vessel 13 and comprises a tine carrier 23, which is vertically adjustable and is provided with tines 23', which are adapted to be immersed below the liquid level 24 in the pulping vessel 13 so that they can catch lightweight substances. The tine carrier 23 is pivotally movable from its immersed position shown in solid lines in FIG. 4 to the position shown in dotted lines outside the pulping vessel so that lightweight substances which have been caught will then fall from the tines onto a shredder 25 for their further processing, by which they are sufficiently disintegrated for being dewatered on a vibrating classifier 26, which is disposed below the shredder 25. The water which drips from the vibrating sorting apparatus 26 is returned by a pump 27 to the pulping vessel 13, see FIG. 4. The separated lightweight substances are then dropped into a bin 28, in which they are carried away.

When the lightweight substances have been removed from the pulping vessel 13, the latter is ready to receive a new batch of the crude garbage or other waste material after the crude suspension has been pumped by a pump 29 through the sieve plate 17 and has been fed into a stirred reactor 30 for a thermal and chemical pretreatment. By that thermal and chemical pretreatment the content of dissolved organic substances in the liquid phase is increased and the suspension is pasteurized and is rendered more effectively dewaterable. The thermal and chemical pretreatment can be conducted at temperatures of 50° to 90° C. and is preferably effected under alkaline conditions at 60° to 70° C. An alkaline solution 31 preferably of sodium hydroxide is added so that fats will be saponified to a water-soluble form.

After the thermal and chemical pretreatment the suspension is transferred by a pump 32 to a suspension storage tank 33, from which the suspension is continuously fed by a metering pump 34 to a solid-liquid separator 35, from which the organic substances which are dissolved in water and have been dissolved by the pretreatment are fed by a pump 36 into a storage tank 37. As the suspension is dewatered, the previously dissolved organic substances are separated and are immediately supplied to the methane reactor. The resulting liquid stream has a concentration of 20 to 40 g COD (chemical oxygen demand) per liter and a residual content of less than 1% suspended solids.

The solids which have been dewatered in the solid-liquid separator 35 now consist predominantly of insoluble carbohydrates, fats, proteins, cellulose, and lignocellulose and are fed by a pulp pump 38 into a solids-hydrolyzing reactor 39, which may be operated in the mesophilic of thermophilic temperature range. By the hydrolysis of solids the biopolymers are decomposed by special hydrolyzing microorganisms to soluble compounds. The solids are mixed with process water, which is taken from a storage tank for process water 41 by a pump 40, to provide a stirrable suspension.

During the hydrolysis the suspension is continuously fed by a pump 42 into the solid-liquid separator 35, in which the products of the hydrolysis are separated for being fed into a methane reactor 43 for producing biogas.

The suspension which contains only a small amount of hydrolyzates is fed by a pump 44 into a second solid-liquid separator 45 and is dewatered therein. The dewatered solids 46 may be subjected to an aerobic composting process and can be used for soil conditioning. The liquid which has been separated in the solid-liquid separator 45 is fed by a pump 47 into the storage tank 37 and is mixed therein with the liquid stream from the solids hydrolyzing reactor.

The organic substances dissolved in water are continuously fed into the methane reactor 43 from the storage tank 37 by a metering pump 48 and by the methane bacteria are converted to the biogas 49, which consists of methane and carbon dioxide and is withdrawn from the top of the methane reactor 43 and delivered to a location where the gas is utilized. The effluent drained from the methane reactor 43 is collected in the storage tank of process water 41 and is fed by a pump 50 to the pulping vessel 13 and used therein to pulp the waste material or crude garbage. Besides, process water is fed by the pump 40 into the solid hydrolyzing reactor 39, as has been described hereinbefore.

Figure 3:
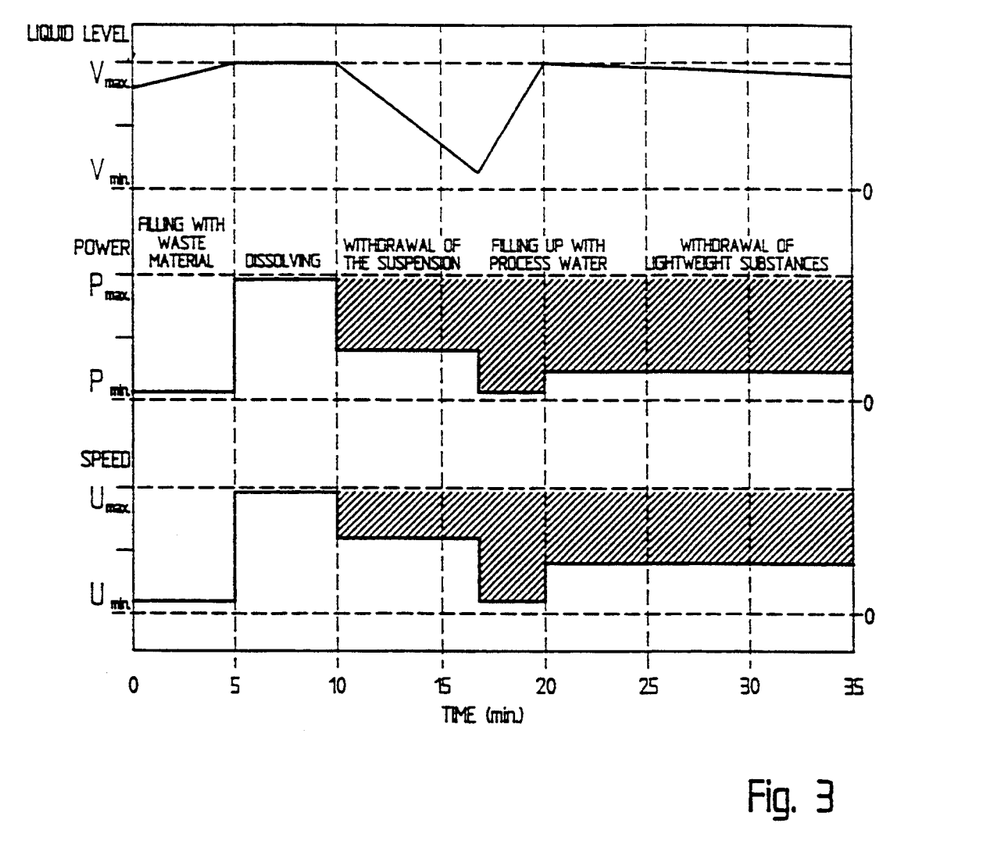
FIG. 3 is a chart illustrating the operation of the pulping vessel and indicating the liquid level, the power consumption, and the speed during various operating periods as a function of time.

The pretreating stage included in the process in accordance with the invention will be explained more in detail hereinafter. A batch of crude waste is supplied to a pulping vessel 13. FIG. 3 illustrates a sequence of operating periods of the impeller 14 with records of the speed, the power consumption and the liquid level as a function of time. FIG. 3 illustrates a cycle of operations performed to process one batch; that cycle is repeated for each charge.

To improve the mixing of the water and waste material in the pulping vessel 13 the contents of the pulping vessel 13 are agitated in that the impeller 14 is rotated at a low speed. The quantity of the batch is so selected that the solids content in the pulping vessel 13 is about 10%. With the timing illustrated by way of example in FIG. 3 that first operating period takes about 5 minutes. Owing to the low speed of the impeller only a very low power consumption at the lower limit which can be used, will be required during that first operating period.

When the entire batch has been charged into the pulping vessel 13 the organic substances are dissolved or defibrated while the impeller 14 rotates at a high speed. As a result, solid organic substances are suspended and soluble substances contained in the cells, such as sugar, are dissolved. Specifically, the fatty acids formed by spontaneously initiated microbial processes when waste materials are stored for several days will be dissolved. The resulting suspension has a COD (dissolved) content of 10 to 35 g/l. Additional organic substances amounting to 80 to 100 g/l remain undissolved and are included in a suspension. Because the impeller 14 produces a toroidal flow, which is radially outwardly directed at the bottom and has only a small axial flow component, hydraulic shearing forces are exerted in the suspension and are utilized to defibrate the biogenic organic substances which have been softened. Owing to the high speed of the impeller 14 a high power consumption is utilized during that second operating period.

After only a few minutes, e.g. in accordance with FIG. 3 after 5 minutes, the concentration of the soluble organic substances in the suspension has risen to a saturation value. A prolongation of the high-power consuming pulping beyond that time would not result in a further increase of the concentration of dissolved substances and would also involve a risk of an undesired disintegration of non-digestable solids. 5 to 15 minutes are required for the pulping in practice.

After the dissolving operation the suspension is pumped by the pump 29 through the sieve plate 17 into the stirred reactor 31. Those components which have not been dissolved, mainly plastics, leather, and wood, are retained by the sieve plate 17. During the pumping the speed of the impeller 14 is reduced so that an undesired disintegration will be avoided and energy will be saved because only a lower power consumption is now required, as is apparent from FIG. 3.

The pulping vessel 13 is subsequently filled up with process water while the impeller 14 is rotated at a low speed. The process water is withdrawn from the storage tank of process water 41 by the pump 50 and during normal operation consists of the effluent of the methane reactor 43, in which the organic substances which have been dissolved in the pulping vessel 13 or hydrolyzed in the solids hydrolyzing reactor are reacted to produce methane and carbon dioxide.

During the addition of the process water the heavy substances in the pulping vessel 13 are collected and by the flowing liquid are entrained into the now open lock chamber 18 for heavy solids. A drain controller, not shown, which is operated only during that operating period, causes the lock chamber 18 for heavy solids to be closed by the shutter 19 in the predetermined intervals of time. The contents of the lock chamber 18 for heavy solids are then washed with water and are drained in that the bottom shutter 20 is opened. When the bottom shutter 20 has been closed and the top shutter 19 has been opened, the lock chamber 18 for heavy solids is ready again to receive heavy solids. The heavy solids discharged into the bin 21 are collected therein and will be disposed of when said bin 21 has been filled.

In the following table the composition of heavy solids separated in the described process is stated. To determine the composition, the contents of the lock chamber for heavy solids were removed after the pulping of a batch and were sorted by hand and subsequently dried.

| Fraction | Dry weight kg | Content % |
| --- | --- | --- |
| Large stones (>10 mm) | 1.24 | 8.3 |
| Stones (<10 mm) | 1.72 | 11.5 |
| Blend (<10 mm) | 7.40 | 49.6 |
| Clay, brick | 1.77 | 11.9 |
| Glass | 1.57 | 10.5 |
| Bone | 0.43 | 2.9 |
| Batteries | 0.06 | 0.4 |
| Ferrous metals | 0.59 | 4.0 |
| Other metals | 0.14 | 0.9 |
| Total | 14.92 | 100.00 |

The lightweight substances are removed by means of the raking device 22, which is suitable for this special application. Because the density of the materials of which the lightweight substances are composed differs only slightly from the density of water they rise to the surface or float in the liquid so that the tine carrier 23 for removing the lightweight substances can be lowered by means of an electric or hydraulic drive into the pulping vessel 13 to such a depth that it is entirely disposed under the surface of the water. The free cross-section of the pulping vessel 13 between the impeller 14 and the wall of the pulping vessel 13 is occupied as completely as possible by the tine carrier 23, which is constituted by a frame provided with transverse struts, on which the tines 23' are mounted, which have a length of 10 to 15 cm and are spaced 5 to 7 cm apart and extend at right angles to the transverse struts.

The geometry of the motion of the raking device 22 is so designed that the rake can be removed from the pulping vessel 13 and that movement will not cause the lightweight substances grasped by the rake to fall down. Only when the rake is disposed outside the pulping vessel 13 and the tine carrier 23 is turned to a horizontal position are the lightweight substances thrown off. The motion is imparted to the raking device 22 by a fully automatic sequence controller, which is not turned off until only insignificant quantities of the lightweight substances are still held by the tines 23'.

A typical composition of the lightweight substances separated by means of the described process is stated in the following table.

| Sorted Fraction | Proportion, kg | Moist % | Content, kg | Dry % | Water Content % | Volatile Solids % |
| --- | --- | --- | --- | --- | --- | --- |
| Plastics | 70.98 | 26.1 | 36.85 | 31.5 | 48.4 | 88.2 |
| Textiles | 43.50 | 16.0 | 12.67 | 10.8 | 70.8 | 87.0 |
| Native organic matter | 13.05 | 4.8 | 2.76 | 2.4 | 79.8 | 89.4 |
| Wood, bone, inert matter | 27.02 | 9.9 | 14.05 | 12.0 | 47.9 | |
| Glass | 0.46 | 0.2 | 0.46 | 0.4 | 10.7 | |
| Hard plastic | 7.56 | 2.7 | 7.14 | 6.1 | 5.2 | |
| Metals | 4.12 | 1.5 | 3.45 | 2.9 | 16.6 | |
| Fines | 50.37 | 18.5 | 21.42 | 18.3 | 57.9 | 58.5 |
| Unsortable residue | 54.95 | 20.2 | 18.19 | 15.6 | 66.9 | 80.0 |

When the lightweight substances have been removed from the pulping vessel 13 the latter is ready to receive a new batch of waste material. The lightweight substances are thrown into the bin 28 immediately or after they have been treated in the shredder 25 and on the vibrating classifier 26.

When the suspension has been removed the speed of the impeller 14 is reduced to a first intermediate speed, which is close to the minimum speed employed during the first period, in which the vessel has been filled up with process water. As a result, the required power consumption is also distinctly reduced. The second period, in which the pulping vessel 13 is filled up with process water, again takes about 5 minutes. During that second period and during the succeeding removal of the lightweight substances by means of the raking device 22 the impeller 14 is operated at a second intermediate speed, which is between the first intermediate speed adopted during the withdrawal of the suspension and the initial speed adopted during the charging of waste material. The saving of energy compared to the operation without such a speed control can be estimated from the hatched area in FIG. 3 and will essentially depend on the proportion of the lightweight substances and will be the larger the longer the time is that is required for a complete removal of the lightweight substances. For instance, the power required to drive the impeller 14 in a pulping vessel 13 having a capacity of 4 $m^3$ is about 10 to 15 $kW/m^3$ for the dissolving period whereas only 2.5 to 3 $kW/m^3$ will be required during the mixing period in which the lightweight substances are removed. The following table indicates the effectiveness of the process which has been described. The amounts of the non-digestable substances which have been removed (heavy and lightweight substances) are compared with the amounts which have been removed when the same waste material was sorted by hand. The removal of each fraction is almost 100%. This means that a high proportion of the non-digestable substances can be removed by the described process.

| Fraction | Glass kg | Metals kg | Minerals kg | Plastics kg | Textiles kg | Wood kg |
|---|---|---|---|---|---|---|
| Amount removed | | | | | | |
| By presorting | 3.4 | 3.3 | 0.8 | 0.7 | | |
| As heavy solids | 0.8 | 0.4 | 2.6 | | | |
| As raked-off lightweight substances | 0.1 | 0.8 | | 10.8 | 3.1 | 3.4 |
| Total | 4.3 | 4.5 | 3.4 | 11.5 | 3.1 | 3.4 |
| Amount recovered by manual sorting | 4.7 | 4.5 | 3.9 | 9.2 | 2.6 | 3.8 |
| Yield | 0.91 | 1.0 | 0.87 | 1.25 | 1.2 | 0.89 |

The yield indicates the ratio of the weight of each fraction which has been mechanically separated in the apparatus to the weight of the same fraction recovered by hand-picking. The two batches used for the comparison were obtained by a taking of representative samples from the same supply of waste materials. The deviations from 100% are within a permissible range of 20% and are due to the inevitable inhomogenity of the waste materials.

In the following table, results are compiled which are typical for the thermal and chemical treatment of the wet waste (fraction of the domestic waste which is gained when dry recyclables like paper, glass, metals and plastics are collected separately) and source separated organic waste in the stirred reactor 30. The thermal and chemical treatment results in a further dissolving of the organic solids (OS) and in a comparison with the original waste material increases the content of neutral detergent fibre (NDF), which is a measure of the substances which can easily be converted by biochemical processes.

| Substrate | Feed of NaOH g NaOH/kg solids | Dissolution of OS | NDF content | pH value |
|---|---|---|---|---|
| Wet Waste | 15–50 | 17% | 55% | 7–9 |
| Source Separated Organic Waste | 14–45 | 14% | 45% | 6.3 |

The amount which is dissolved by the thermal and chemical treatment can be controlled by the temperature which is selected for the treatment. In the following table, typical values for the increase of the content of organic substances in solution are stated as the COD and the solids contents for various operating temperatures.

| | Temperature % | Increase of COD in solution % | Increase of dissolved organic solids % |
|---|---|---|---|
| Wet Waste | 65 | 18 | 26 |
| | 70 | 50 | 71 |
| Source Separated Organic Waste | 65 | 6 | 1 |
| | 70 | 23 | 54 |

By the dewatering of the suspension in the solid-liquid separation stage 35 the previously dissolved organic substances are removed and are immediately supplied to the methane reactor 43. A liquid stream is formed, which has a concentration of 10 to 40 g COD/l and contains less than 1% undissolved solids. Typical values for the amount of dissolved organic solid residue (OSR) produced by the hydrolysis in the solids hydrolyzing reactor 39 and the decrease of the content of organic substances (OS) in percent are compiled in the following table.

| Dilution rate 1/d | Hydrolysis Time h | Production of Dissolved OSR % | Decrease of OS content % |
|---|---|---|---|
| 1.5 | 49.5 | 19.34 | 64.25 |
| 1.5 | 70.5 | 45.33 | 85.89 |
| 1.5 | 49.3 | 66.78 | 93.91 |
| 2.0 | 23.2 | 16.50 | 18.04 |
| 2.0 | 44.5 | 17.23 | 43.47 |
| 2.0 | 47.0 | 16.42 | 74.84 |
| 1.0 | 42.5 | 58.50 | 76.89 |
| 1.0 | 20.0 | 55.14 | 66.62 |

Figure 5:
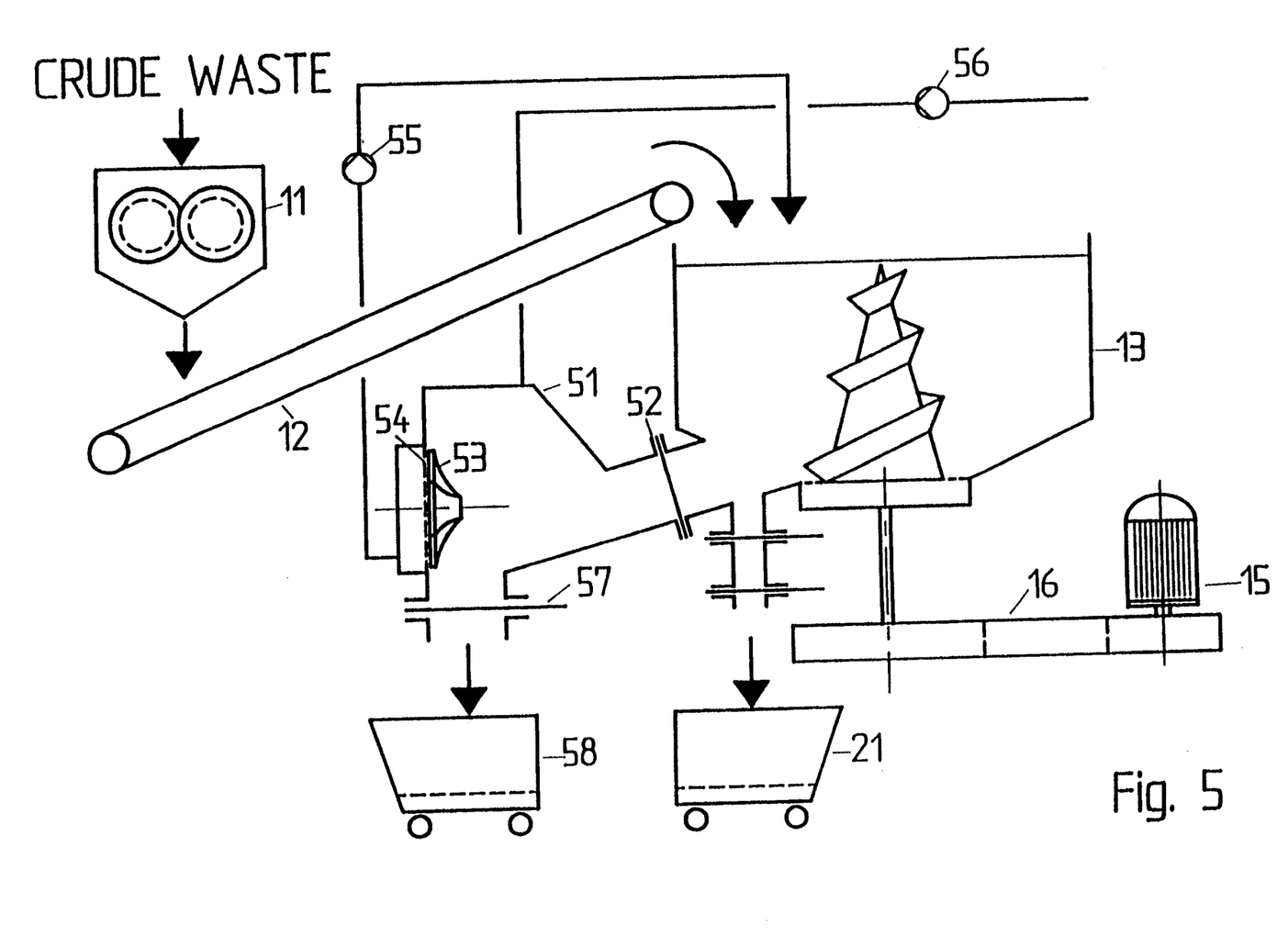
FIG. 5 is a schematic representation showing the pulping vessel, which instead of the raking device illustrated in FIG. 4 is provided with a washing compartment.

An alternate embodiment is now described with reference to FIG. 5. Instead of the raking device 22 which has been described, a washing compartment 51 may be used to remove the lightweight substances and may either immediately succeed the pulping vessel 13 or may be connected to it by a line. The washing compartment 51 comprises a closed vessel, which can be connected to the pulping vessel 13 from time to time by a gate valve 52.

When the crude suspension has been removed from the pulping vessel 13, the lightweight substances are entrained by process water from the pulping vessel 13 into the washing compartment 51 when the gate valve 52 has been opened. The washing compartment 51 contains an approximately vertical impeller 53, which is mounted on a horizontal shaft. Behind the impeller 53, a perforated sieve 54 formed with slots is provided and a thin fibre-containing suspension is removed through said sieve 54 by a pump 55. In case of need, a pump 56 can subsequently be operated to feed additional process water as a rinsing water and an additional fibre-containing suspension can then be pumped off. The dilute suspension which has been pumped from the washing compartment 51 constitutes a part of the water which is used to dissolve the next batch in the pulping vessel 13. The lightweight substances can be removed from the washing compartment 51 through a gate valve 57 and can be collected and carried away in a container 58.

Just as the use of the raking device bin 22 shown in FIG. 4, the use of the washing compartment results in a low power consumption. The power required to drive the impeller 53 is equal to the power required to drive the impeller 14 in the pulping vessel 13 and the operation of the latter impeller is continued during the operation of the raking device 22 whereas in the alternative embodiment comprising the washing compartment 51 the impeller 14 in the pulping vessel 13 need not be operated to discharge lightweight substances.

The use of the washing compartment 51 will be particularly desirable in the processing of waste materials in which the fibrous organic substances are blended intimately with the lightweight substances and the desired separation cannot be achieved when the raking device 22 is employed.

We claim:

1. A process of treating waste and/or waste-like mixtures for anaerobic digestion of biogenic-organic substances, comprising the following process steps:
preparing an easily dewaterable suspension of biogenic-organic substances by mechanical treatment of waste and/or waste-like mixtures in a pulping vessel which contains a rotatable impeller; the mechanical treatment comprising blending waste and/or waste-like mixtures and water and subsequently or consecutively selectively dissolving and/or defibrating said biogenic-organic substances with a controlled action of flow-dynamical forces; wherein the flow-dynamical forces are formed by said rotatable impeller and the speed of the impeller is controlled so the substances contained in the waste and/or waste-like mixtures which are not suitable for anaerobic digestion are not subject an appreciable disintegration by the mechanical treatment.

2. The process according to claim 1, wherein said rotating impeller generates a toroidal or loop-shaped flow in the pulping vessel.

3. The process according to claim 1, further comprising removing said suspension containing the dissolved and/or defibrated biogenic-organic substances through sieve means.

4. The process according to claim 1, further comprising:
(i) skimming off or separating light-weight substances with a raking device associated with said pulping vessel, said raking device comprising a tine carrier having tines, wherein said skimming off or separating said light-weight substances comprises the steps of:
(A) adjusting said tine carrier vertically so that said tines can catch said lightweight substances;
(B) moving said raking device out of said pulping vessel to remove said lightweight substances; and
(C) tilting said tine carrier to throw off said lightweight substances.

5. The process according to claim 4, further comprising shredding said lightweight substances obtained in (C) to reduce the size of said lightweight substances and rinsing off any residual fibrous material still adhering to said lightweight substances with a vibratory sorter.

6. The process according to claim 5, further comprising:
transferring said lightweight substances obtained in (C) together with water into a washing compartment containing a vertically oriented impeller;
washing said lightweight substances to remove any fibrous material still adhering to said lightweight substances; and
withdrawing said fibrous material from said washing compartment through a sieve and pumping said fibrous material back to said pulping vessel.

7. A process of treating waste and/or waste-like mixtures for anaerobic digestion of biogenic-organic substances, comprising the following process steps:
preparing an easily dewaterable suspension of biogenic-organic substances by mechanical treatment of waste and/or waste-like mixtures in a pretreating stage; the mechanical treatment comprising blending waste and/or waste-like mixtures and water and subsequently or consecutively selectively dissolving and/or defibrating said biogenic-organic substances with a controlled action of flow-dynamical forces; wherein the flow-dynamical forces are controlled so that the substances contained in the waste and/or waste-like mixtures which are not suitable for anaerobic digestion are not subject to an appreciable disintegration by the mechanical treatment.

8. The process according to claim 7, further comprising converting at least a part of said suspension of biogenic-organic substances to biogas and compost-like residual substances by an anaerobic digestion process.

9. The process according to claim 7, further comprising
(i) a solid-liquid separating stage of dividing said suspension of biogenic-organic substances into a liquid stream containing water soluble organic substances and a solids-laden stream;
(ii) subjecting said liquid stream to methane fermentation; and
(iii) subjecting said solids-laden stream to an aerobic composting.

10. The process according to claim 9, wherein the ratio of said biogenic-organic substances in said easily dewaterable suspension to its solids content exceeds the ratio of biogenic-organic substances to solids in the waste and/or waste-like mixtures.

11. The process according to claim 7, further comprising the steps of:
(i) withdrawing at least a portion of said suspension of biogenic-organic substances;
(ii) slurring the remaining substances which are not suitable for anaerobic digestion with water;
(iii) removing the heavy solids from the mixture of part ii; and
(iv) separating lightweight substances from the mixture of (iii).

12. The process according to claim 11, wherein said lightweight substances obtained in (iv) are subjected to an additional cleaning treatment with water to remove fibrous material adhering to said lightweight substances, and said fibrous material is returned to said pretreating stage.

13. The process according to claim 11, wherein said lightweight substances obtained in (iv) are reduced in size and subjected to a cleaning treatment.

14. The process according to claim 13, wherein recyclable materials are separated from said cleaned lightweight substances.

15. The process according to claim 13, wherein said cleaned light weight substances are compacted and dewatered by compacting means and the water which has been squeezed out is returned to said pretreating stage.

16. The process according to claim 7, wherein said mechanical treatment is performed in a pulping vessel, said pulping vessel containing a rotating impeller, wherein the speed of said rotating impeller is selected to effect a gentle treatment of the substances contained in the waste and/or waste like mixtures which are not suitable for anaerobic digestion.

17. The process according to claim 16, wherein said impeller is operated at a high speed during said dissolving and/or defibrating of said biogenic-organic substances and at a reduced speed during the removal of said substances which are not suitable for anaerobic digestion.

18. The process according to claim 7, wherein said action of flow-dynamical forces causes a toroidal or loop-shaped flow during at least the beginning of said dissolving and/or defibrating of said biogenic-organic substances.

19. The process according to claim 7, wherein the pH of said suspension of biogenic-organic substances is adjusted to be alkaline and said alkaline suspension is heated to a temperature of between 40° C. to 90° C. for up to 12 hours.

20. The process according to claim 7, wherein said process further comprises:
   (i) a solid-liquid separating stage of dividing said suspension of biogenic-organic substances into a liquid stream containing water-soluble organic substances and a solids-laden stream containing a solids content of less than 50% by weight;
   (ii) subjecting said liquid stream to methane fermentation;
   (iii) subjecting said solids-laden stream to an anaerobic hydrolysis of solids in the mesophilic or thermophilic temperature range; and
   (iv) subjecting the resulting hydrolyzate from (iii) to a methane fermentation.

21. The process according to claim 7, wherein the process further comprises:
   (i) a solid-liquid separating stage of dividing said suspension of biogenic-organic substances into a liquid stream containing water-soluble organic substances and a solids-laden stream, said solids-laden stream comprising fiber-containing solids which are organic;
   (ii) converting said fiber-containing solids to soluble organic substances in a solids hydrolyzing reactor having at least one stage, wherein the hydrolysis is effected by adding extraneous enzymes, said enzymes being produced either in a reactor which is connected in parallel or as a result of an inoculation of the solids with special microorganisms, wherein said hydrolysis produces dissolved organic substances; and
   (iii) continuously or intermittently removing said dissolved substances from (ii) and subjecting to methane fermentation.

22. The process according to claim 21, wherein step (ii) comprises additional mechanical, chemical or thermal treatments or a combination of such treatments to increase the hydrozability of said fiber-containing solids and to facilitate the separation of non-hydrolyzable solids for said dissolved organic substances.

23. The process according to claim 7 wherein the ratio of said biogenic-organic substances in said easily dewaterable suspension to its solids content exceeds the ratio of biogenic-organic substances to solids in the waste and/or waste-like mixtures.

24. The process according to claim 7 further comprising the steps of:
   i) withdrawing at least a portion of said suspension of biogenic-organic substances;
   ii) slurrying the remaining substances which are not suitable for anaerobic digestion with water; and
   iii) removing the heavy solids and separating lightweight substances from the mixture of ii).

* * * * *